(12) United States Patent
Sebastian et al.

(10) Patent No.: US 11,672,420 B2
(45) Date of Patent: **\*Jun. 13, 2023**

(54) SYSTEM AND METHOD FOR TRACKING MOTION

(71) Applicant: Aeva, Inc., Mountain View, CA (US)

(72) Inventors: Richard L. Sebastian, Frederick, MD (US); Kendall L. Belsley, Falls Church, VA (US)

(73) Assignee: Aeva, Inc., Mountain View, CA (US)

( * ) Notice: Subject to any disclaimer, the term of this patent is extended or adjusted under 35 U.S.C. 154(b) by 191 days.

This patent is subject to a terminal disclaimer.

(21) Appl. No.: 17/062,596

(22) Filed: Oct. 4, 2020

(65) Prior Publication Data

US 2021/0259544 A1 Aug. 26, 2021

Related U.S. Application Data

(63) Continuation of application No. 16/258,613, filed on Jan. 27, 2019, now Pat. No. 10,791,925, which is a continuation of application No. 15/667,935, filed on Aug. 3, 2017, now Pat. No. 10,188,290, which is a continuation of application No. 14/986,640, filed on Jan. 1, 2016, now Pat. No. 9,723,980, which is a continuation of application No. 14/265,465, filed on
(Continued)

(51) Int. Cl.
| | | |
|---|---|---|
| *A61B 3/113* | (2006.01) |
| *A61B 3/00* | (2006.01) |
| *G01S 13/88* | (2006.01) |
| *G01S 17/88* | (2006.01) |
| *G01S 17/86* | (2020.01) |
| *A61B 3/14* | (2006.01) |
| *A61B 5/00* | (2006.01) |
| *A61B 5/11* | (2006.01) |

(52) U.S. Cl.
CPC ............... *A61B 3/113* (2013.01); *A61B 3/00* (2013.01); *A61B 3/14* (2013.01); *A61B 3/145* (2013.01); *A61B 5/0077* (2013.01); *A61B 5/11* (2013.01); *G01S 13/88* (2013.01); *G01S 17/86* (2020.01); *G01S 17/88* (2013.01)

(58) Field of Classification Search
CPC .. A61B 3/113; A61B 3/00; A61B 3/14; A61B 3/145; A61B 5/0077; A61B 5/11; G01S 13/88; G01S 17/86; G01S 17/88
See application file for complete search history.

(56) References Cited

U.S. PATENT DOCUMENTS

| | | | |
|---|---|---|---|
| 8,757,804 B2 * | 6/2014 | Sebastian | ................ G01S 17/86 351/205 |
| 9,723,980 B2 * | 8/2017 | Sebastian | ................ A61B 3/14 |

(Continued)

*Primary Examiner* — James C. Jones
(74) *Attorney, Agent, or Firm* — Toering Patents PLLC

(57) ABSTRACT

Detecting position information related to a face, and more particularly to an eyeball in a face, using a detection and ranging system, such as a Radio Detection And Ranging ("RADAR") system, or a Light Detection And Ranging ("LIDAR") system. The position information may include a location of the eyeball, translational motion information related to the eyeball (e.g., displacement, velocity, acceleration, jerk, etc.), rotational motion information related to the eyeball (e.g., rotational displacement, rotational velocity, rotational acceleration, etc.) as the eyeball rotates within its socket.

15 Claims, 6 Drawing Sheets

Related U.S. Application Data

Apr. 30, 2014, now abandoned, which is a continuation of application No. 14/076,158, filed on Nov. 8, 2013, now Pat. No. 8,757,804, which is a continuation of application No. 13/470,715, filed on May 14, 2012, now Pat. No. 8,579,439, which is a continuation of application No. 12/762,772, filed on Apr. 19, 2010, now Pat. No. 8,177,363, which is a continuation of application No. 11/610,867, filed on Dec. 14, 2006, now Pat. No. 7,699,469.

(60) Provisional application No. 60/750,045, filed on Dec. 14, 2005.

(56) References Cited

U.S. PATENT DOCUMENTS

| | | | |
|---|---|---|---|
| 10,188,290 B2* | 1/2019 | Sebastian | A61B 5/11 |
| 10,791,925 B2* | 10/2020 | Sebastian | G01S 17/88 |
| 2005/0119560 A1* | 6/2005 | Mostafavi | A61B 6/463 |
| | | | 600/425 |

* cited by examiner

SYSTEM AND METHOD FOR TRACKING MOTION

RELATED APPLICATIONS

This Application is a continuation application of application Ser. No. 16/258,613, which was filed on Jan. 27, 2019, now U.S. Pat. No. 10,791,925; which in turn is continuation of application Ser. No. 15/667,935, which was filed on Aug. 3, 2017, now U.S. Pat. No. 10,188,290; which in turn is a continuation of application Ser. No. 14/986,640, which was filed on Jan. 1, 2016, now U.S. Pat. No. 9,723,980; which in turn is a continuation of application Ser. No. 14/265,465, which was filed on Apr. 30, 2014, now abandoned; which in turn is a continuation of application Ser. No. 14/076,158, which was filed on Nov. 8, 2013, now U.S. Pat. No. 8,757,804; which in turn is a continuation of application Ser. No. 13/470,715, which was filed on May 14, 2012, now U.S. Pat. No. 8,579,439; which in turn is a continuation of application Ser. No. 12/762,772, which was filed on Apr. 19, 2010, now U.S. Pat. No. 8,177,363; which in turn is a continuation of application Ser. No. 11/610,867, which was filed on Dec. 14, 2006, now U.S. Pat. No. 7,699,469; and claims priority from U.S. Provisional Patent Application No. 60/750,045, entitled "System and Method for Tracking Eyeball Motion," filed Dec. 14, 2005. The contents of all of the foregoing applications are incorporated herein by reference. This application is related to U.S. Provisional Patent Application No. 60/651,989, entitled "Chirped Coherent Laser Radar System and Method," filed Feb. 14, 2005, the contents of which are also incorporated herein by reference.

FIELD OF THE INVENTION

The invention relates generally to tracking the movement of an eyeball, and more particularly to tracking the movement of an eyeball using a detection and ranging system.

BACKGROUND OF THE INVENTION

Determining the motion of an eyeball of an individual may have practical application in a multitude of environments. For example, eyeball motion may be monitored in iris and/or corneal recognition systems, stimulus response measurement, medical procedures, virtual reality systems, or other environments. Eyeball motion information may enable improved imaging of the eyeball, iris or retinal. Eyeball motion information may also enable imaging of the eyeball, iris, or cornea at greater ranges than would otherwise be possible.

However, conventional eyeball motion tracking systems, such as stereo systems, may not provide position information related to an eyeball with enough speed and/or accuracy for all of the possible applications of eyeball motion tracking. In general, these systems may also be hampered by an inability to determine position information related to an eyeball from a relatively extended distance.

These and other drawbacks associated with conventional eyeball motion tracking systems and methods exist.

SUMMARY

One aspect of the invention relates to detecting position information related to a face, and more particularly to an eyeball in a face, using a detection and ranging system, such as a Radio Detection And Ranging ("RADAR") system, or a Light Detection And Ranging ("LIDAR") system. The position information may include a location of the eyeball, translational motion information related to the eyeball (e.g., displacement, velocity, acceleration, jerk, etc.), rotational motion information related to the eyeball (e.g., rotational displacement, rotational velocity, rotational acceleration, etc.) as the eyeball rotates within its socket. One of the advantages of the implementation of a detection and ranging system in detecting position information related to the eyeball may include an increased speed at which the position information may be determined. In fact, in some implementations, the determination of the position information may be substantially instantaneous with substantially no latency. Another advantage of the implementation of a detection and ranging system in detecting position information related to the eyeball may include enabling eyeball motion to be determined from an increased distance and/or with a reduced invasiveness to the individual.

As mentioned above, the detection and ranging system may include a coherent LIDAR system. In these implementations, a first set of electromagnetic radiation beams may be incident on the eyeball at one or more locations on the eyeball. The first set of electromagnetic radiation beams may be returned from these locations on the eyeball to the LIDAR system (e.g., via backscattering, reflection, etc.), and the frequency shift of the returned electromagnetic radiation may be measured.

The coherent LIDAR system may determine information related to one or both of location (e.g., x, y, z) and rotational velocity (e.g., a component of the velocity of the surface of the eyeball that is parallel to an incident electromagnetic radiation beam) at each measurement location on the eyeball. If the radius of the eyeball is known, this information may be determined with three measurement beams focused on three separate measurement locations on the eyeball. If the radius is unknown, the radius may be determined with a fourth measurement beam focused on a fourth separate measurement location on the eyeball. Once the eye has been located (e.g., with three measurement beams if the radius is known or with four measurement beams if the radius is not known), the center of the eye and the closest point of the eye may be determined based on the known location.

At individual ones of the measurement locations, a velocity vector representative of the movement of the eyeball within the eye socket that is tangential to the surface of the eyeball may be determined. If a valid determination of this velocity vector is made for at least two measurement locations on the eyeball that are (i) not the closest point and are (ii) not on the same great circle with each other and the closest point, then the rotational motion of the eyeball within its socket may be determined by the LIDAR system. This may enable the tracking of the lateral rotational motion of the eyeball, and by extension the surface features on the eyeball (e.g., the iris, the pupil, etc.). It should be appreciated that the eyeball may not be formed as a perfect sphere, and that asymmetries in the shape of the eyeball may impact the velocity vector that is calculated at a given measurement location on the eyeball. However, eyeball shape in general is close enough to spherical that typically any non-uniformities in the eyeball may be de minimis and, as such, the eyeball may assumed to be perfectly spherical in some embodiments (and for illustrative purposes herein).

In some implementations, lateral or vertical motion of the face that displaces the eye socket, along with the eyeball, may be determined by video optical flow processing of video footage captured by a video imaging system being used in conjunction with the LIDAR system. Rotation in the plane of the image of the video imaging system may also be determined in this manner. Movement (e.g., displacement, rotation, etc.) of the face out of the plane of the images captured by the video imaging system may be determined by the LIDAR system. For example, a second set of electromagnetic beams may be emitted from the LIDAR system to one or more locations on the face (other than the eyeball), and range and range rate measurements of the one or more locations on the face may be made to determine information related to the movement of the face out of the plane of the images captured by the video imaging system.

The relatively low frequency of head motion and the great number of measurements will allow for a relatively high accuracy of head motion determination in this, or some other, manner. This being done, the location and velocity of the 3D center points of the eyeballs may be determined so that the residual motion of the eyeballs in the eye sockets may be determined separate from the motion of the eye sockets, as if the eyeball were in a stationary socket.

Another aspect of various embodiments of the invention may relate to a laser radar system that unambiguously detects a range of a target and a range rate at which the target is moving relative to the laser radar system. Another aspect of various embodiments of the invention may relate to a laser radar system that uses multiple laser radar sections to obtain multiple simultaneous measurements (or substantially so), whereby both range and range rate can be determined without various temporal effects introduced by systems employing single laser sections taking sequential measurements. In addition, other aspects of various embodiments of the invention may enable faster determination of the range and rate of the target, a more accurate determination of the range and rate of the target, and/or may provide other advantages.

In some embodiments of the invention, the laser radar system may emit a first target beam and a second target beam toward a target. The first target beam and the second target beam may be reflected by the target back toward the laser radar system. The laser radar system may receive the reflected first target beam and second target beam, and may determine at least one of a range of the target from the laser radar system, and a range rate of the target. In some embodiments of the invention, the laser radar system may include a first laser radar section, a second laser radar section, and a processor.

In some embodiments of the invention, the first laser radar section may generate a first target beam and a first reference beam. The first target beam and the first reference beam may be generated by a first laser source at a first frequency that may be modulated at a first chirp rate. The first target beam may be directed toward a measurement point on the target. The first laser radar section may combine one portion of the first target beam that may be directed towards, and reflected from, the target. Another portion of the first target beam, referred to as a local oscillator beam, may be directed over a path with a known or otherwise fixed path length. This may result in a combined first target beam.

According to various embodiments of the invention, the second laser radar section may be collocated and fixed with respect to the first laser radar section. More particularly, the relevant optical components for transmitting and receiving the respective laser beams are collocated and fixed. The second laser radar section may generate a second target beam and a second reference beam. The second target beam and the second reference beam may be generated by a second laser source at a second frequency that may be modulated at a second chirp rate. The second chirp rate may be different from the first chirp rate. This may facilitate one or more aspects of downstream processing, such as, signal discrimination, or other aspects of downstream processing. The second target beam may be directed toward the same measurement point on the target as the first target beam. The second laser radar section may combine one portion of the second target beam that may be directed towards, and reflected from, the target, and another portion of the second target beam that may be directed over a path with a known or otherwise fixed path length. This results in a combined second target beam.

According to various embodiments of the invention, the processor receives the first and second combined target beams and measures a beat frequency caused by a difference in path length between each of the respective reflected target beams and its corresponding local oscillator beam, and by any Doppler frequency shift created by target motion relative to the laser radar system. The beat frequencies may then be combined linearly to generate unambiguous determinations of the range and the range rate of the target, so long as the beat frequencies between each of the respective local oscillator beams and the its reflected target beam correspond to simultaneous (or substantially simultaneous) temporal components of the reflected target beams. Simultaneous (or substantially simultaneous) temporal components of the reflected target beams may include temporal components of the target beams that: 1) have been incident on substantially the same portion of the target, 2) have been impacted by similar transmission effects, 3) have been directed by a scanning optical element under substantially the same conditions, and/or 4) share other similarities. The utilization of beat frequencies that correspond to simultaneous (or substantially simultaneous) temporal components of the reflected target beams for linear combination may effectively cancel any noise introduced into the data by environmental or other effects.

Because the combined target beams may be created by separately combining the first local oscillator beam and the second local oscillator beam with different target beams, or different portions of the same target beam, the first combined target beam and the second combined target beam may represent optical signals that might be present in two separate, but coincident, single source frequency modulated laser radar systems, just prior to final processing. For example, the combined target beams may represent optical signals produced by target interferometers in the single source systems.

According to various embodiments, the target beams may be directed to and/or received from the target on separate optical paths. In some embodiments, these optical paths may be similar but distinct. In other embodiments the first target beam and the second target beam may be coupled prior to emission to create a combined target beam that may be directed toward the target along a common optical path. In some embodiments, the target beam may be reflected by the target and may be received by the laser radar system along a reception optical path separate from the common optical path that directed the target beam toward the target. Such embodiments may be labeled "bistatic." Or, the combined target beam may be received by the laser radar system along the common optical path. These latter embodiments may be labeled "monostatic." Monostatic embodiments may provide advantages over their bistatic counterparts when operating with reciprocal optics. More particularly, monostatic embodiments of the invention are less affected by differential Doppler effects and distortion due to speckle, among other things. Differential Doppler effects are created, for example, by a scanning mirror that directs the target beam to different locations on a target. Since different parts of the mirror are moving at different velocities, different parts of the target beam experience different Doppler shifts, which may introduce errors into the range and or range rate measurements. These effects have been investigated and analyzed by Anthony Slotwinski and others, for example, in NASA Langley Contract No. NAS1-18890 (May 1991) Phase II Final Report, Appendix K, submitted by Digital Signal Corporation, 8003 Forbes Place, Springfield, Va. 22131, which is incorporated herein by reference in its entirety.

In some instances, the first laser source and the second laser source may generate electromagnetic radiation at a first carrier frequency and a second carrier frequency, respectively. The first carrier frequency may be substantially the same as the second carrier frequency. This may provide various enhancements to the laser radar system, such as, for example, minimizing distortion due to speckle, or other enhancements.

In some embodiments, the first laser source and the second laser source may provide electromagnetic radiation with highly linearized frequency chirp. To this end, the linearization of the electromagnetic radiation emitted by the first laser source and the second laser source may be calibrated on a frequent basis (e.g. each chirp), or in some embodiments continuously (or substantially so). This linearization the frequency chirp of the electromagnetic radiation may provide enhanced range measurement accuracy, or other enhancements, over conventional systems in which linearization may occur at startup, when an operator notices degraded system performance, when the operator is prompted to initiate linearization based on a potential for degraded performance, or when one or more system parameters fall out of tolerance, etc. Frequent and/or automated linearization may reduce mirror differential Doppler noise effects during high speed scanning and may maximize the effectiveness of dual chirp techniques for canceling out these and other noise contributions to range estimates.

In some embodiments of the invention, the laser radar system may determine the range and the range rate of the target with an increased accuracy when the range of the target from the laser radar system falls within a set of ranges between a minimum range and a maximum range. When the range of the target does not fall within the set of ranges, the accuracy of the laser radar system may be degraded. This degradation may be a result of the coherence length(s) of the first laser source and the second laser source, which is finite in nature. For example, the distance between the minimum range and the maximum range may be a function of the coherence length. The longer the coherence length of the first laser source and the second laser source, the greater the distance between the minimum range and the maximum range. Thus, increasing the coherence length of the first laser source and the second laser source may enhance range and range rate determinations by the laser radar system by providing the ability to make determinations over an enhanced set of ranges.

In some embodiments of the invention, one or both of the first laser source and the second laser source may implement a system and method for controllably chirping electromagnetic radiation from a radiation source. The system and method may enable electromagnetic radiation to be produced at a substantially linear chirp rate with a configurable period. In some embodiments, the radiation may include a single, frequency shifted, resonant mode.

In some embodiments of the invention, a system may include a radiation source, one or more optical elements that form an optical cavity, a frequency shifter, an optical switch and an optical amplifier. In some embodiments, the frequency shifter may be disposed within the optical cavity to receive electromagnetic radiation from the optical cavity, and to output a frequency shifted portion of the received electromagnetic radiation back to the optical cavity. The optical switch may be disposed within the optical cavity to receive electromagnetic radiation from the optical cavity. The optical switch may be controllable to either direct the received electromagnetic radiation away from the optical cavity, or to return the received electromagnetic radiation back to the optical cavity. In some instances, the optical switch may be controllable to couple radiation from the radiation source to the optical cavity while directing the received electromagnetic radiation away from the optical cavity, the radiation from the source being received at the optical switch at an initial frequency.

According to various embodiments of the invention, the optical cavity may be "filled" by directing radiation from the laser source, emitted at the initial frequency, into the optical cavity for a period of time that corresponds to the optical length of the optical cavity. In some embodiments, the radiation from the laser source may be directed into the optical cavity by the optical switch. While the electromagnetic radiation from the laser source is being directed in to the cavity, the optical switch may be controlled to direct radiation received by the optical switch away from the optical cavity, or "dumped" from the cavity. Once the cavity is "filled" (e.g., after the time period corresponding to the optical length of the optical cavity has passed) the flow of radiation from the laser source to the optical cavity may be halted. In some embodiment, the flow of radiation from the laser source to the optical cavity may be halted by powering down the laser source. In other embodiments, the flow of radiation from the laser source to the optical cavity may be halted by controlling the optical switch to dump the radiation from the laser source away from the optical cavity. The radiation injected into the optical cavity while the cavity was being filled, may be circulated within the cavity by the optical switch, which may be controlled to direct radiation received from the optical cavity back into the optical cavity.

In some embodiments of the invention, as the electromagnetic radiation is circulated within the optical cavity, the frequency of the radiation may be incrementally adjusted by the frequency shifter during each trip around the optical cavity. Through this periodic, incremental adjustment, the frequency of the radiation within the optical cavity may be chirped in a substantially linear manner. The rate at which the frequency of the electromagnetic radiation is chirped may be related to one or both of the incremental frequency adjustment applied by the frequency shifter and the optical length of the cavity. Thus, the rate at which the frequency of the radiation is chirped, may be controlled via one or both of these variables.

In some embodiments, a quality factor of the optical cavity may be degraded by various losses within the optical cavity. For example, radiation output from the optical cavity to a device may constitute a loss. Other losses may also be present, such as losses due to imperfections in the optical elements, or other parasitic losses. To combat the degradation of the quality factor, an optical amplifier may be disposed within the optical cavity. The optical amplifier may be selected or controlled to provide enough gain to radiation within the optical cavity to overcome the sum of the cavity losses so that a predetermined or controlled intensity of radiation output from the optical cavity may be maintained. The optical amplifier may also be selected based on one or more other characteristics, such as, for example, homogeneous line width, gain bandwidth, or other specifications.

In some embodiments of the invention, one of the chirp rates may be set equal to zero. In other words, one of the laser sources may emit radiation at a constant frequency. This may enable the laser source emitting at a constant frequency to be implemented with a simpler design, a small footprint, a lighter weight, a decreased cost, or other enhancements that may provide advantages to the overall system. In these embodiments, the laser radar section with chirp rate set equal to zero may be used to determine only the range rate of the target.

In some embodiments of the invention, the processor may linearly combine the first combined target beam and the second combined target beam digitally to generate the range signal and the range rate signal. For example, the processor may include a first detector and a second detector. The first detector may receive the first combined target beam and may generate a first analog signal that corresponds to the first combined target beam. The first analog signal may be converted to a first digital signal by a first converter. The processor may include a first frequency data module that may determine a first set of frequency data that corresponds to one or more frequency components of the first digital signal.

The second detector may receive the second combined target beam and may generate a second analog signal that corresponds to the second combined target beam. The second analog signal may be converted to a second digital signal by a second converter. The processor may include a second frequency data module that may determine a second set of frequency data that corresponds to one or more frequency components of the second digital signal.

The first set of frequency data and the second set of frequency data may be received by a frequency data combination module. The frequency data combination module may generate a range rate signal and a range signal derived from the first set of frequency data and the second set of frequency data.

In other embodiments of the invention, the processor may mix the first combined target beam and the second combined target beam electronically to generate the range signal and the range rate signal. For example, the processor may include a modulator. The modulator may multiply the first analog signal generated by the first detector and the second analog signal generated by the second detector to create a combined analog signal. In such embodiments, the processor may include a first filter and a second filter that receive the combined analog signal. The first filter may filter the combined analog signal to generate a first filtered signal. The first filtered signal may be converted by a first converter to generate a range rate signal. The second filter may filter the combined analog signal to generate a second filtered signal. The second filtered signal may be converted by a second converter to generate a range signal.

According to other embodiments of the invention, the processor may mix the first combined target beam and the second combined target beam optically to generate the range signal and the range rate signal. For example, the processor may include a detector that receives the first combined target beam and the second combined target beam and generates a combined analog signal based on the detection of the first combined target beam and the second combined target beam. In such embodiments, the processor may include a first filter and a second filter that receive the combined analog signal. The first filter may filter the combined analog signal to generate a first filtered signal. The first filtered signal may be converted by a first converter to generate a range rate signal. The second filter may filter the combined analog signal to generate a second filtered signal. The second filtered signal may be converted by a second converter to generate a range signal.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION

Figure 1:
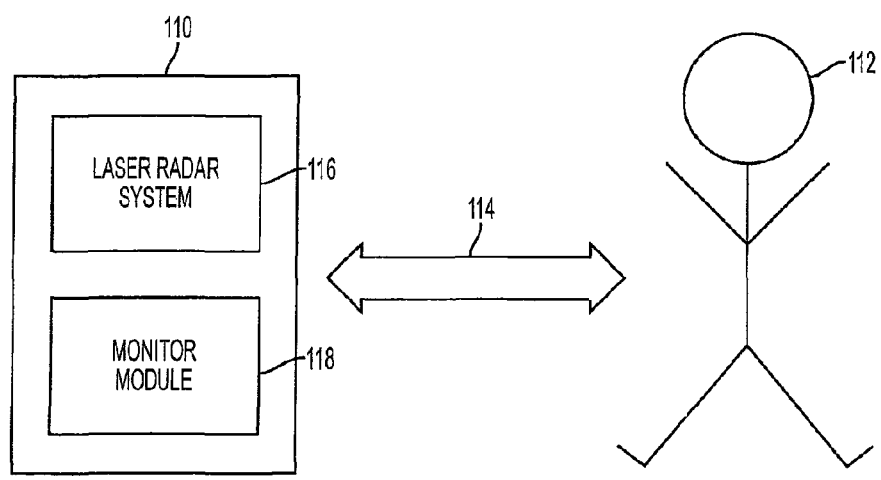
FIG. 1 illustrates a system for monitoring motion of an eyeball of an individual according to one or more embodiments of the invention.

FIG. 1 is an exemplary illustration of a system 110 for detecting position information related to a face, and more particularly to an eyeball in a face of an individual 112, in accordance with some embodiments of the invention. System 110 may determine position information related to the eyeball of individual 112. System 110 may include a laser radar system 116 capable of determining a range to and/or a range rate (i.e., velocity) of a point on a surface of individual 112 (e.g., skin, clothing, lips, etc.). System 110 may include a monitor module 118 capable of determining position information related to the eyeball of individual 112 based on the determinations of laser radar system 116. System 110 may enable the position information related to the eyeball of individual 112 to be monitored and determined remotely from individual 112 without directly contacting individual 112.

In some embodiments of the invention, laser radar system 116 may direct a beam of electromagnetic radiation 114 toward individual 112 to be incident on individual 112 at a point on the surface of individual 112 to be measured. Some or all of radiation 114 directed to the point on the surface of individual 112 may be reflected by the surface, and may then be received back into laser radar system 116. As described below, based on one or more aspects of radiation 114 (e.g., frequency, phase, intensity, etc.) prior to emission and/or subsequent to reflection, laser radar system 116 may determine one or both of the range and the range rate of the point on the surface with respect to laser radar system 116.

According to various embodiments of the invention, laser radar system 116 may make a plurality of determinations of range and/or range rate of a set of measurement points on a surface of the eyeball of individual 112 (e.g., at a periodic rate) over a period of time. Monitor module 118 may implement the determined ranges and range rates to determine the position information related to the eyeball.

According to various embodiments of the invention, monitor module 118 may additionally monitor movement of the head of individual 112, in order to more accurately determine position information related to the eyeball of individual 112. In some of these embodiments, system 110 may include a video imaging system that captured video footage (successive images) of individual 112. Lateral or vertical motion of the face of individual 112 (in the plane of the images captured by the video imaging system) that displaces the eye socket, along with the eyeball, may be determined by video optical flow processing (or some other motion tracking processing) of the video footage captured by the video imaging system. Similarly, the rotation of the face of individual 112 within the image plane may be determined. In this way, three degrees of motion may be measured by the video imaging system. This optical flow processing may be performed by monitor module 118. Motion of the face of individual 112 out of the plane of the images captured by the video imaging system may be determined by taking measurements of the face (outside of the eye sockets) by laser radar system 116. These motions comprise range motion (a translational degree of freedom) and the two rotational degrees of freedom that are orthogonal to the image plane of the video imaging system. Thus, by combining the information determined from the video footage captured by the video imaging system and the measurements of laser radar system 116, monitor module 118 may determine the motion of the face of individual 112 in six degrees of freedom.

By determining the motion of the face of individual 112, monitor module 118 may track the motion and/or position of the eye socket of individual 112. Monitor module 118 may adjust determinations of the position and/or movement of the eyeball of individual 112, using the motion and/or position of the eye socket of individual 112, to reflect only (or substantially only) the rotation of the eyeball in the eye socket.

Figure 2:
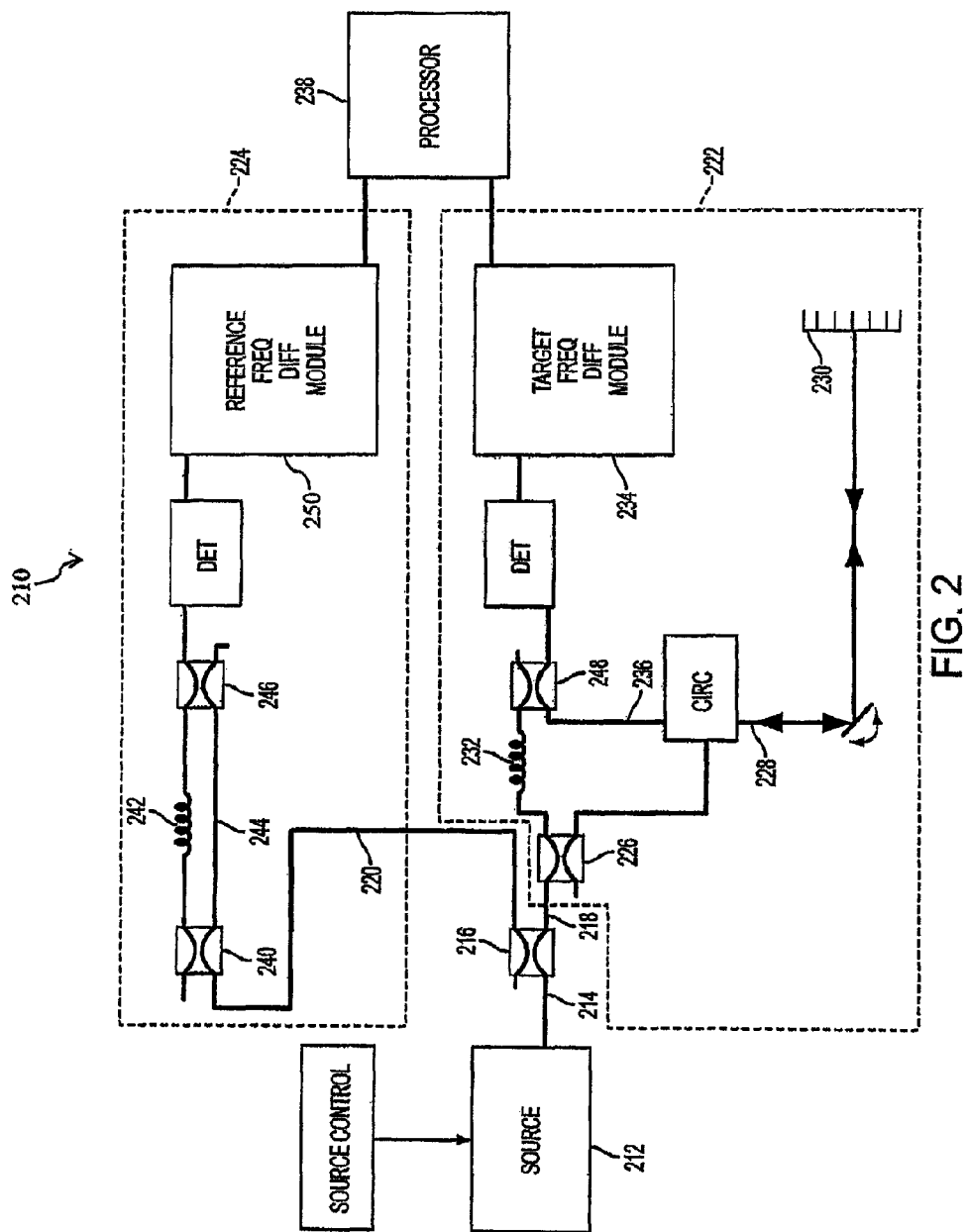
FIG. 2 illustrates a laser radar system that may be implemented in the system for monitoring an eyeball of an individual according to one or more embodiments of the invention.

FIG. 2 illustrates a frequency modulated laser radar system 210 that may be implemented within system 110 as laser radar system 116, according to some embodiments of the invention. System 210 may include a laser source 212 that emits a beam 214 of electromagnetic radiation. Beam 214 may be emitted at a frequency that is continuously varied, or chirped. In some instances, chirping the frequency may include sweeping the frequency between a lower frequency and an upper frequency (or vice versa) in a periodic manner (e.g. a sawtooth waveform, a triangle waveform, etc.). Beam 214 may be divided by an optical coupler 216 into a target beam 218 and a reference beam 220. It should be appreciated that although laser radar system 210 is shown and described as a single beam system, that in order to provide beams of electromagnetic radiation to a plurality of points on the eyeball of the individual beam 214 may be divided into a plurality of beams, and each beam may then be subsequently processed in the manner described below.

In conventional embodiments, system 210 may include a target interferometer 222 and a reference interferometer 224. Target interferometer 222 may receive target beam 218, and may divide the target beam at an optical coupler 226. Target interferometer 222 is typically used to generate a target signal that may depend upon a range of a target 230 (e.g. individual 112) from target interferometer 222. Target interferometer may accomplish this by directing one portion 228 of target beam 218 toward target 230, and the other portion 232 of target beam 218 to a target frequency difference module 234 over an optical path with a fixed path length. Portion 228 of target beam 218 may be reflected by target 230 and may be transmitted to target frequency difference module 234 via optical coupler 226 and an optical fiber 236. Based on interference between portions 236 and 232 at coupler 248, target frequency difference module 234 may generate the target signal corresponding to a beat frequency of portions 236 and 232 of target beam 218 due to the difference between their path lengths.

According to various embodiments of the invention, reference interferometer 224 may receive reference beam 220 and may generate a reference signal corresponding to a frequency difference between two portions of reference beam 224 that may be directed over two separate fixed paths with a known path length difference. More particularly, reference beam 220 may be divided by an optical coupler 240 into a first portion 242 and a second portion 244. First portion 242 may have a fixed optical path length difference relative to second portion 244. Based on interference between portions 242 and 244 at coupler 246, reference frequency difference module 250 may generate the reference signal corresponding to a beat frequency of portions 242 and 244 of reference beam 220 caused by the fixed difference between their path lengths.

As will be appreciated, target interferometer 222 and reference interferometer 224 have been illustrated and described as Mach-Zehnder interferometers. However other interferometer configurations may be utilized. For example, target interferometer 222 and reference interferometer 224 may include embodiments wherein Michelson-Morley interferometers may be formed.

In some embodiments, system 210 may include a processor 238. Processor 238 may receive the target signal and the reference signal and may process these signals to determine the range of target 230. Range information determined based on the target signal and the reference signal may be used to determine a range rate of target 230 with respect to target interferometer 222.

Figure 3:
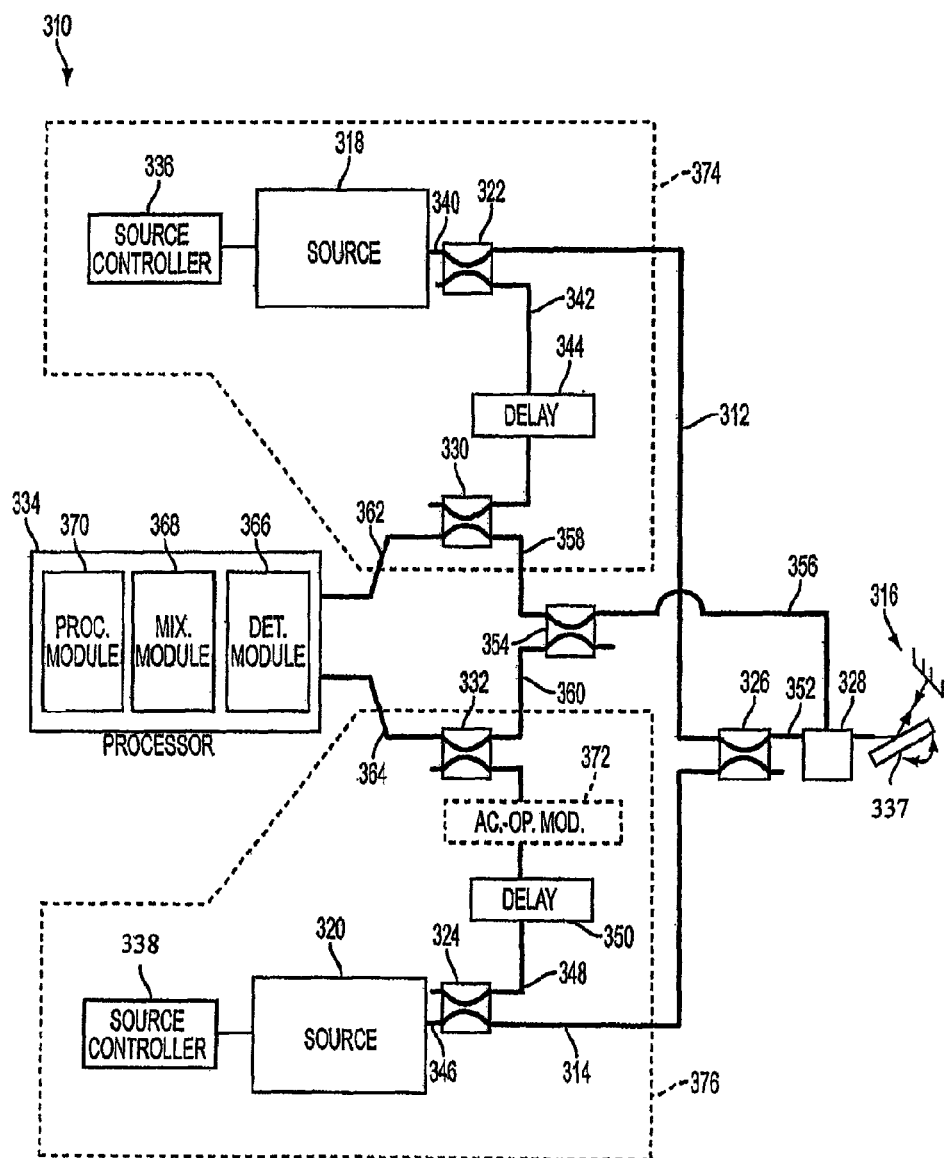
FIG. 3 illustrates a laser radar system that may be implemented in the system for monitoring an eyeball of individual according to one or more embodiments of the invention.

FIG. 3 illustrates an exemplary embodiment of a laser radar system 310 that may be implemented within system 110, as laser radar system 116, to monitor one or more points on a surface of the eyeball of individual 112, according to some embodiments of the invention. Laser radar system 310 may employ two or more laser radar sections, each of which emits a target beam of radiation toward a target. For example, a first laser radar section 374 emits a first target beam 312 and a second laser radar section 376 emits a second target beam 314 toward a target 316 (e.g., individual 112). In some embodiments of the invention, first target beam 312 and second target beam 314 may be chirped to create a dual chirp system. The implementation of laser radar system 310 in system 110 to monitor one or more points on a surface of the eyeball of individual 112 may provide unambiguous determinations of the range and the range rate of the points on the surface of the eyeball of individual 112 with respect to system 110, and may enable enhanced determinations of position information related to the eyeball of individual 112 by monitoring module 118. For example, the unambiguous determination of the range and/or the range rate of the points on the surface of the eyeball of individual 112 may reduce an amount of noise in the determined ranges and/or range rates. If present, the noise may impact the accuracy of the determinations of the ranges and/or range rates. Inaccuracies within the determined ranges and/or range rates may hamper determinations that leverage the determined ranges and/or range rates to position information related to the eyeball of individual 112.

It should be appreciated that although laser radar system 310 is shown and described as a dual beam system that provides two beams incident on a single point, that this description is not limiting and that in order to provide monitor a plurality of points on the eyeball each of the target beams may be divided into a plurality of beams, and each beam may then be subsequently processed in the manner described below. In some implementations, the plurality of points on the eyeball may be monitored by successively by the single point radiation (e.g., by scanning the single point of radiation to each of the plurality of points on the eyeball in succession). Although in these implementations the points on the eyeball may not be monitored absolutely simultaneously, the single point radiation may be provided to each of the plurality of points on the eyeball quickly enough that the resulting collection of data may be processed as if the plurality of points had been monitored simultaneously. In some implementations, a hybrid approach may be implemented in which the beams provided by laser radar system 310 as a single point of radiation may be divided to provide a plurality of points of radiation, and each of the plurality of points of radiation may be scanned successively to different points on the eyeball (and/or individual 112).

According to various embodiments of the invention, laser section 374 may include a laser source controller 336, a first laser source 318, a first optical coupler 322, a first beam delay 344, a first local oscillator optical coupler 330, and/or other components. Second laser radar section 376 may include a laser source controller 338, a second laser source 320, a second optical coupler 324, a second beam delay 350, a second local oscillator optical coupler 332 and/or other components. For example, some or all of the components of each of laser radar sections 374 and 376 may be obtained as a coherent laser radar system from Metris USA. Coherent laser radar systems from Metris USA may provide various advantages, such as enhanced linearity functionality, enhanced phase wandering correction, and other advantages to laser radar system 310 in determining the range and the range rate of target 316.

In some embodiments of the invention, first target beam 312 and second target beam 314 may be reflected by target 316 back toward laser radar system 310. Laser radar system 310 may receive first target beam 312 and second target beam 314, and may determine at least one of a range of target 316 from laser radar system 310, and a range rate of target 316.

According to various embodiments of the invention, first laser source 318 may have a first carrier frequency. First laser source 318 may emit a first laser beam 340 at a first frequency. The first frequency may be modulated at a first chirp rate. The first frequency may be modulated electrically, mechanically, acousto-optically, or otherwise modulated as would be apparent. First laser beam 340 may be divided by first optical coupler 322 into first target beam 312 and a first local oscillator beam 342. First local oscillator beam 342 may be held for a first delay period at a first beam delay 344.

In some embodiments of the invention, second laser source 320 may emit a second laser beam 346 at a second frequency. The second frequency may be modulated at a second chirp rate different from the first chirp rate. The second frequency may be modulated electrically, mechanically, acousto-optically, or otherwise modulated. The first chirp rate and the second chirp rate may create a counter chirp between first laser beam 340 and second laser beam 346.

In some instances, the second carrier frequency may be substantially the same as the first carrier frequency. For example, in some embodiments the percentage difference between the first baseline frequency and the second baseline frequency is less than 0.05%. This may provide various enhancements to laser system 310, such as, for example, minimizing distortion due to speckle, or other enhancements. Second laser beam 346 may be divided by second optical coupler 324 into a second target beam 314 and a second local oscillator beam 348. Second local oscillator beam 348 may be held for a second delay period at a second beam delay 350. The second delay period may be different than the first delay period.

In some embodiments, the output(s) of first laser source 318 and/or second laser source 320 (e.g. first laser beam 340 and/or second laser beam 346) may be linearized using mechanisms provided in, for example, Metris USA Model MV200. Phase wandering of the output(s) of first laser source 318 and/or second laser source 320 may be corrected using mechanisms provided in, for instance, Metris USA Model MV200.

In some embodiments of the invention, laser radar system 310 may determine the range and the range rate of target 316 with an increased accuracy when the range of target 316 from laser radar system 310 falls within a set of ranges between a minimum range and a maximum range. When the range of target 316 does not fall within the set of ranges, the accuracy of laser radar system 310 may be degraded.

According to various embodiments of the invention, first beam delay 344 and second beam delay 350 may be adjustable. Adjusting first beam delay 344 and second beam delay 350 may enable laser radar system 310 to be adjusted to bring the set of ranges over which more accurate determinations may be made closer to, or further away from, laser radar system 310. First beam delay 344 and the second beam delay 350 may be adjusted to ensure that the range of target 316 falls within the set of ranges between the minimum range and the maximum range so that the range and the range rate of target 316 may be determined accurately. First beam delay 344 and second beam delay 350 may be adjusted by a user, or in an automated manner.

The degradation of determinations of range and range rate when the range of target 316 is outside of the set of ranges may be a result of the finite nature of the coherence length of first laser source 318 and second laser source 320. For example, the distance between the minimum range and the maximum range may be a function of the coherence length. The longer the coherence length of first laser source 318 and second laser source 320, the greater the distance between the minimum range and the maximum range may be. Thus, increasing the coherence length of first laser source 318 and second laser source 320 may enhance range and range rate determinations by laser radar system 310 by providing the ability to make determinations over an enhanced set of ranges.

In some embodiments of the invention, first local oscillator beam 342 may be divided into a plurality of first local oscillator beams and second local oscillator beam 348 may be divided into a plurality of second local oscillator beams. In such instances, laser radar system 310 may include a plurality of beam delays that may apply delays of varying delay periods to the plurality of first local oscillator beams and the plurality of second local oscillator beams. This may ensure that one of the plurality of first local oscillator beams and one of the plurality of second local oscillator beams may have been delayed for delay periods that may enable the range and range rate of the target to be determined accurately.

Accordingly, in some embodiments of the invention, first laser source 318 and second laser source 320 may emit chirped electromagnetic radiation with an enhanced coherence length. For example, first laser source 318 and/or second laser source 320 may include system 310 as illustrated in FIG. 3 and described above.

According to various embodiments, first target beam 312 and second target beam 314 may be directed and/or received from target 316 on separate optical paths. In some embodiments, these optical paths may be similar but distinct. In other embodiments, first target beam 312 and second target beam 314 may be coupled by a target optical coupler 326 into a combined target beam 352 prior to emission that may be directed toward target 316 along a common optical path. In some embodiments, combined target beam 352 (or first target beam 312 and second target beam 314, if directed toward target 316 separately) may be reflected by target 316 and may be received by laser radar system 310 along a reception optical path separate from the common optical path that directed combined target beam 352 toward target 316. Such embodiments may be labeled "bistatic." Or, combined target beam 352 may be received by laser radar system 310 as a reflected target beam 356 along the common optical path. These latter embodiments may be labeled "monostatic." Monostatic embodiments may provide advantages over their bistatic counterparts when operating with reciprocal optics. In monostatic embodiments, the common optical path may include optical member 328 that may provide a common port for emitting combined target beam 352 and receiving reflected target beam 356. Optical member 328 may include an optical circulator, an optical coupler or other optical member as may be apparent.

In some embodiments, the common optical path may include a scanning element 337. Scanning element 337 may include an optical element such as, for instance, a mirror, a lens, an antenna, or other optical elements that may be oscillated, rotated, or otherwise actuated to enable combined target beam 352 to scan target 316. In some instances, scanning element 337 may enable scanning at high speeds. In conventional systems, scanning elements may be a source of mirror differential Doppler noise effects due to speckle or other optical effects that may degrade the accuracy of these systems. However, because various embodiments of laser radar system 310 use simultaneous measurements (or substantially so) to unambiguously determine range and range rate, inaccuracies otherwise induced by high speed scanning may be avoided.

In some embodiments of the invention, a target optical coupler 354 may divide reflected target beam 356 into a first reflected target beam portion 358 and a second reflected target beam portion 360. First local oscillator optical coupler 330 may combine first local oscillator beam 342 with first reflected target beam portion 358 into a first combined target beam 362. Second local oscillator optical coupler 332 may combine second local oscillator beam 348 with second reflected target beam portion 360 into a second combined target beam 364. In some embodiments not shown in the drawings, where, for example first target beam 312 and second target beam 314 may be directed to and/or received from target 316 separately, first local oscillator optical coupler 330 may combine first target beam 312 that is reflected with first local oscillator beam 342 to create first combined target beam 362, and second target beam 314 that is reflected may be combined with second local oscillator beam 348 to create second combined target beam 364.

Because first local oscillator beam 342 and second local oscillator beam 348 may be combined with different target beams, or different portions of the same target beam (e.g. reflected target beam 356), first combined target beam 362 and second combined target beam 364 may represent optical signals that might be present in two separate, but coincident, single laser source frequency modulated laser radar systems, just prior to final processing. For example, laser source controller 336, first laser source 318, first optical coupler 322, first beam delay 344, and first local oscillator optical coupler 330 may be viewed as a first laser radar section 374 that may generate first combined target beam 362 separate from second combined target beam 364 that may be generated by a second laser radar section 376. Second laser radar section 376 may include laser source controller 338, second laser source 320, second optical coupler 324, second beam delay 350, and second local oscillator optical coupler 332.

In some embodiments, laser radar system 310 may include a processor 334. Processor 334 may include a detection module 366, a mixing module 368, a processing module 370, and/or other modules. The modules may be implemented in hardware (including optical and detection components), software, firmware, or a combination of hardware, software, and/or firmware. Processor 334 may receive first combined target beam 362 and second combined target beam 364. Based on first combined target beam 362 and second combined target beam 364, processor 334 may generate the range signal and the range rate signal. Based on the range signal and the range rate signal, the range and the range rate of target 316 may be unambiguously determined.

In some embodiments of the invention, processor 334 may determine a first beat frequency of first combined local oscillator beam 362. The first beat frequency may include a difference in frequency, attributable to a difference in path length, of first local oscillator beam 342 and the component of reflected target beam 356 that corresponds to first target beam 312 that has been reflected from target 316. Processor 334 may determine a second beat frequency of second combined local oscillator beam 364. The second beat frequency may include a difference in frequency, attributable to a difference in path length, of second local oscillator beam 348 and the component of reflected target beam 356 that corresponds to second target beam 314 that has been reflected from target 316. The first beat frequency and the second beat frequency may be determined simultaneously (or substantially so) to cancel noise introduced by environmental or other effects. One or more steps may be taken to enable the first beat frequency and the second beat frequency to be distinguished from other frequency components within first combined target beam 362, other frequency components within second combined target beam 364, and/or each other. For example, these measures may include using two separate chirp rates as the first chirp rate and the second chirp rate, delaying first local oscillator beam 342 and second local oscillator beam 350 for different delay times at first beam delay 344 and second beam delay 350, respectively, or other measures may be taken.

It will be appreciated that while FIG. 3 illustrates an exemplary embodiment of the invention implemented primarily using optical fibers and optical couplers, this embodiment is in no way intended to be limiting. Alternate embodiments within the scope of the invention exist in which other optical elements such as, for example, prisms, mirrors, half-mirrors, beam splitters, dichroic films, dichroic prisms, lenses, or other optical elements may be used to direct, combine, direct, focus, diffuse, amplify, or otherwise process electromagnetic radiation.

According to various embodiments of the invention, processor 334 may mix first combined target beam 362 and second combined target beam 364 to produce a mixed signal. The mixed signal may include a beat frequency sum component that may correspond to the sum of the first beat frequency and the second beat frequency, and a beat frequency difference component that may correspond to the difference between the first beat frequency and the second beat frequency. For a target having constant velocity, first laser beam 340 and second laser beam 346 beat frequencies may be described as follows:

$$f_1(t) = \frac{4\pi v}{\lambda_1} + 2\pi\gamma_1(R - RO_1), \text{ and} \quad (1)$$

$$f_2(t) = \frac{4\pi v}{\lambda_2} + 2\pi\gamma_2(R - RO_2), \text{ respectively}, \quad (2)$$

where $f_1(t)$ represents the first beat frequency, $f_2(t)$ represents the second beat frequency, $\lambda_1$ and $\lambda_2$ are the two optical wavelengths, v is the target velocity, $\gamma_1$ and $\gamma_2$ are proportional to the respective chirp rates, R is the measured range and $RO_1$ and $RO_2$ represent the range offsets for the two laser radars. Now assume that $\lambda_1=\lambda_2=\lambda$. We may subtract the equations to yield $$f_1(t)-f_2(t)=2\pi R(\gamma_1-\gamma_2)-2\pi(\gamma_1 RO_1-\gamma_2 RO_2) \quad (3)$$

Rearranging (3) we obtain $$R = \frac{(f_1(t) - f_2(t))}{2\pi(\gamma_1 - \gamma_2)} + \frac{(\gamma_1 RO_1 - \gamma_2 RO_2)}{(\gamma_1 - \gamma_2)} \quad (4)$$

as the corrected range measurement. Similarly we may combine (1) and (2) to obtain the expression, $$v = \frac{\lambda}{4\pi}\left(\frac{f_1(t) - \frac{\gamma_1}{\gamma_2}f_2(t)}{1 - \frac{\gamma_1}{\gamma_2}}\right) + \frac{\lambda\gamma_1}{2}\left(\frac{RO_1 - RO_2}{1 - \frac{\gamma_1}{\gamma_2}}\right), \quad (5)$$

which provides a measure of the target velocity.

According to various embodiments of the invention, the beat frequency sum component, described above in Equation 4, may be filtered from the mixed signal to produce a range signal. From the beat frequency sum component included in the range signal (e.g. f1(t)+f2(t), a determination of the distance from laser radar system 310 to target 316 may be made. The determination based on the range signal may be unambiguous, and may not depend on either the instantaneous behavior, or the average behavior of the Doppler frequency shift (e.g. v/λ).

In some embodiments, the beat frequency difference component, described above in Equation 4, may be filtered from the mixed signal to produce a range rate signal. From the beat frequency difference component included in the range rate signal, a determination of the range rate of target 316 may be unambiguously made. To determine the range rate of target 316, $$f_1(t) - \frac{\gamma_1}{\gamma_2}f_2(t)$$

may be represented as a value proportional to a chirp rate difference between the first chirp rate and the second chirp rate. This may enable the Doppler shift information to be extracted, which may represent an instantaneous velocity (i.e., range rate) of target 316.

In some embodiments of the invention, the second chirp rate may be set to zero. In other words, second laser source 318 may emit radiation at a constant frequency. This may enable second laser source 318 to be implemented with a simpler design, a small footprint, a lighter weight, a decreased cost, or other enhancements that may provide advantages to the overall system. In such embodiments, laser radar system 310 may include a frequency shifting device. The frequency shifting device may include an acousto-optical modulator 372, or other device. Acousto-optical modulator 372 may provide a frequency offset to second local oscillator beam 348, which may enhance downstream processing. For example, the frequency offset may enable a stationary target beat frequency between second local oscillator beam 348 and second reflected target beam portion 360 representative of a range rate of a stationary target to be offset from zero so that the a direction of the target's movement, as well as a magnitude of the rate of the movement, may be determined from the beat frequency. This embodiment of the invention has the further advantage that it may allow for continuous monitoring of the target range rate, uninterrupted by chirp turn-around or fly-back. Chirp turn-around or fly-back may create time intervals during which accurate measurements may be impossible for a chirped laser radar section. In these embodiments, laser radar section 376 may only determine the range rate of target 316 while laser radar system 310 retains the ability to measure both range and range rate.

Figure 4:
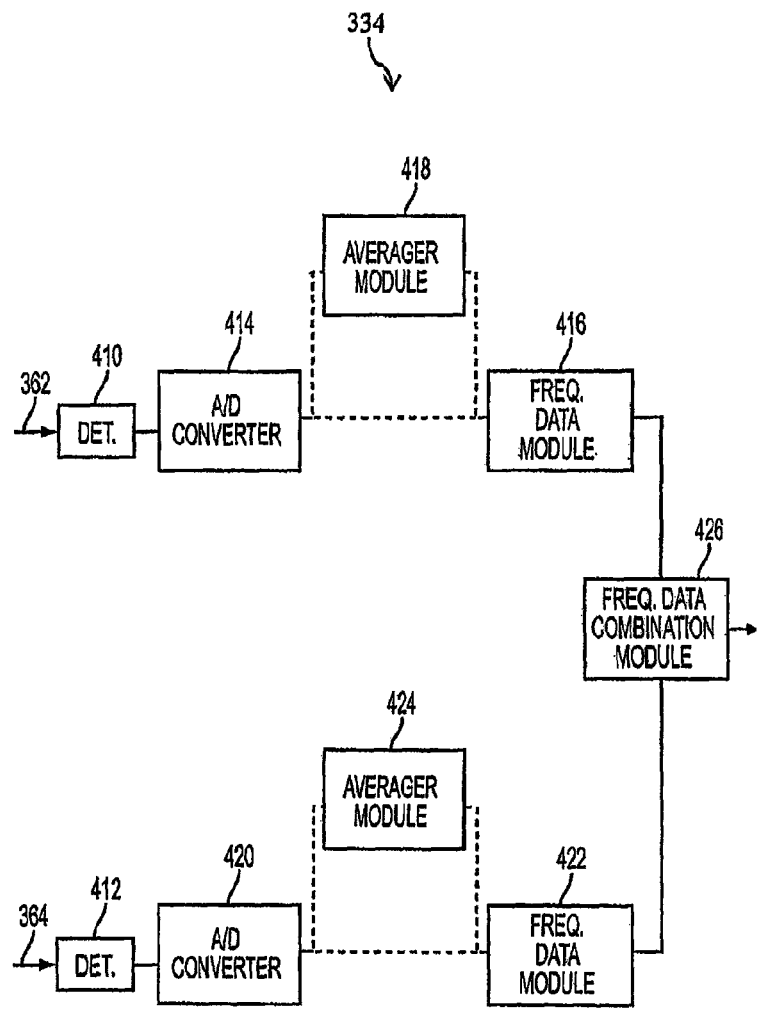
FIG. 4 illustrates a processor that digitally mixes two combined target beams according to one or more embodiments of the invention.

FIG. 4 illustrates a processor 334 according to one embodiment of the invention. Processor 334 may mix first combined target beam 362 and second combined target beam 364 digitally. For example, processor 334 may include a first detector 410 and a second detector 412. The first detector 410 may receive first combined target beam 362 and may generate a first analog signal that corresponds to first combined target beam 362. The first analog signal may be converted to a first digital signal by a first converter 414. Processor 334 may include a first frequency data module 416 that may determine a first set of frequency data that corresponds to one or more frequency components of the first digital signal. In some instances, the first digital signal may be averaged at a first averager module 418. In such instances, the averaged first digital signal may then be transmitted to first frequency data module 416.

Second detector 412 may receive second combined target beam 364 and may generate a second analog signal that corresponds to second combined target beam 364. The second analog signal may be converted to a second digital signal by a second converter 420. Processor 334 may include a second frequency data module 422 that may determine a second set of frequency data that corresponds to one or more of frequency components of the second digital signal. In some instances, the second digital signal may be averaged at a second averager module 424. In such instances, the averaged second digital signal may then be transmitted to second frequency data module 422.

The first set of frequency data and the second set of frequency data may be received by a frequency data combination module 426. Frequency data combination module 426 may linearly combine the first set of frequency data and the second set of frequency data, and may generate a range rate signal and a range signal derived from the mixed frequency data.

Figure 5:
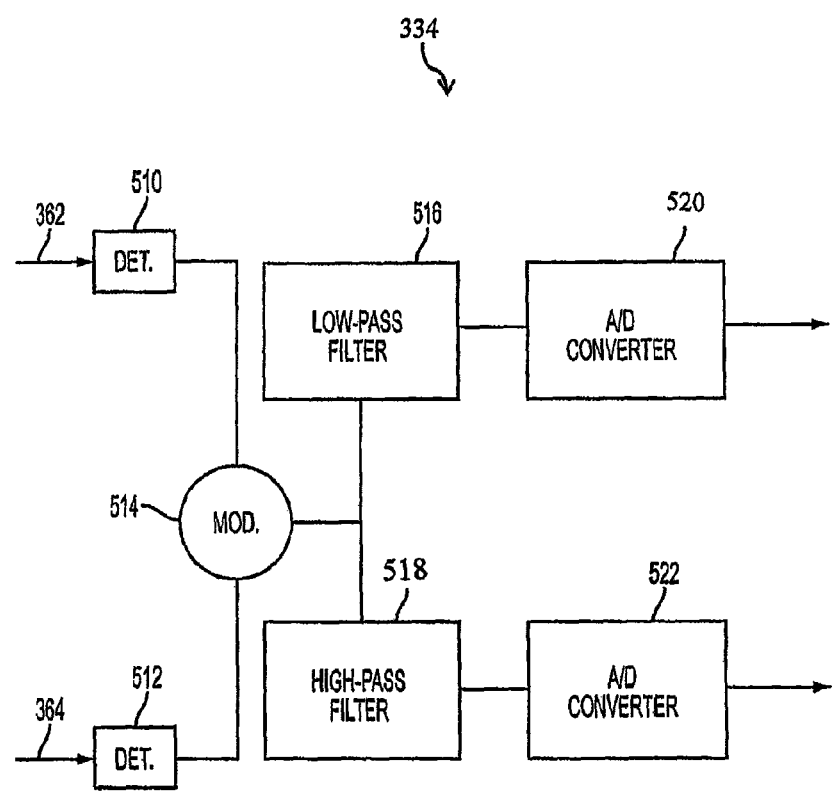
FIG. 5 illustrates a processor that electrically mixes two combined target beams according to one or more embodiments of the invention.

FIG. 5 illustrates a processor 334 according to another embodiment of the invention. Processor 334 may include a first detector 510 and a second detector 512 that may receive first combined target beam 362 and second combined target beam 364, respectively. First detector 510 and second detector 512 may generate a first analog signal and a second analog signal associated with first combined target beam 362 and second combined target beam 364, respectively. Processor 334 may mix first combined target beam 362 and second combined target beam 364 electronically to generate the range signal and the range rate signal. For example, processor 334 may include a modulator 514. Modulator 514 may multiply the first analog signal generated by first detector 510 and the second analog signal generated by second detector 512 to create a combined analog signal. In such embodiments, processor 334 may include a first filter 516 and a second filter 518 that receive the combined analog signal. First filter 516 may filter the combined analog signal to generate a first filtered signal. In some instances, first filter 516 may include a low-pass filter. The first filtered signal may be converted by a first converter 520 to generate the range rate signal. Second filter 518 may filter the combined analog signal to generate a second filtered signal. For instance, second filter 518 may include a high-pass filter. The second filtered signal may be converted by a second converter 522 to generate the range signal.

Figure 6:
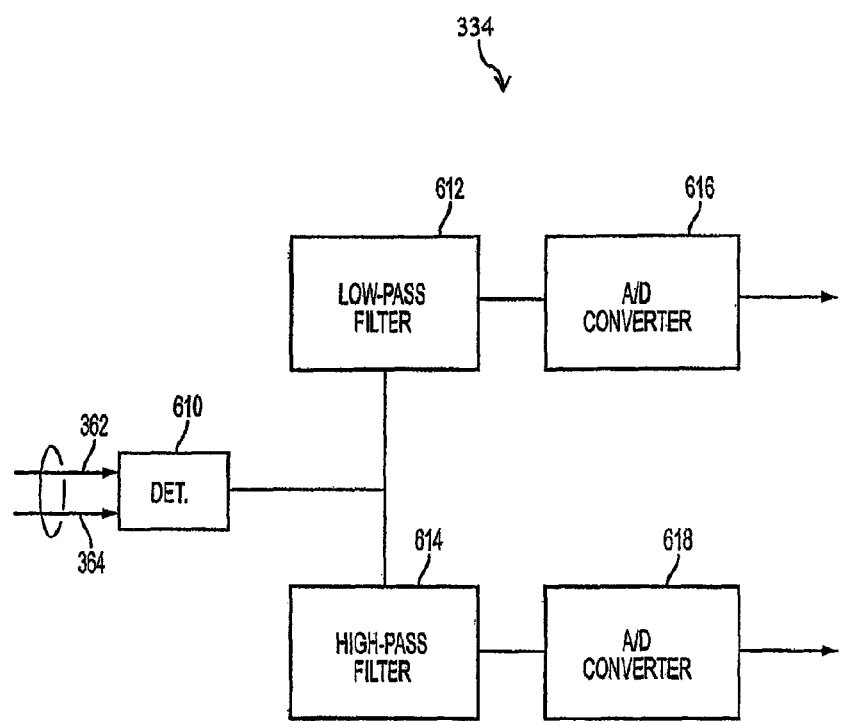
FIG. 6 illustrates a processor that optically mixes two combined target beams according to one or more embodiments of the invention.

FIG. 6 illustrates a processor 334 according to yet another embodiment of the invention. Processor 334 may mix first combined target beam 362 and second combined target beam 364 optically to generate the range signal and the range rate signal. For example, processor 334 may include a detector 610 that receives first combined target beam 362 and second combined target beam 364 and generates a combined analog signal based on the detection. In such embodiments, processor 334 may include a first filter 612 and a second filter 614 that receive the combined analog signal. First filter 612 may filter the combined analog signal to generate a first filtered signal. First filter 612 may include a low-pass filter. The first filtered signal may be converted by a first converter 616 to generate the range rate signal. Second filter 614 may filter the combined analog signal to generate a second filtered signal. Second filter 14 may include a high-pass filter. The second filtered signal may be converted by a second converter 618 to generate the range signal.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A system for determining motion of a target, the system comprising:
a video imaging system configured to capture a plurality of images of the target;
a lidar system configured to generate a range measurement or a Doppler velocity measurement for a point on the target; and
a processor configured to:
determine, from the plurality of images of the target, at least one first aspect of motion of the target based on the plurality of images of the target,
determine, from the range measurement or the Doppler velocity measurement, at least one second aspect of motion of the target, wherein the at least one first aspect of motion of the target is orthogonal to the at least one second aspect of motion of the target, and
combine the at least one first aspect of motion of the target and the at least one second aspect of motion of the target to determine the motion of the target.

2. The system of claim 1, wherein the at least one first aspect of motion comprises a lateral motion of the target in an image plane of the plurality of images of the target, a vertical motion of the target in the image plane of the plurality of images of the target, or a rotation of the target in the image plane of the plurality of images of the target.

3. The system of claim 1, wherein the processor configured to determine, from the plurality of images of the target, at least one first aspect of motion of the target based on the plurality of images of the target comprises the processor configured to determine at least three first aspects of motion of the target based on the plurality of images of the target.

4. The system of claim 3, wherein the at least three first aspects of motion comprises a lateral motion of the target in an image plane of the plurality of images of the target, a vertical motion of the target in the image plane of the plurality of images of the target, and a rotation of the target in the image plane of the plurality of images of the target.

5. The system of claim 1, wherein the lidar system is configured to generate the range measurement, and wherein the at least one second aspect of motion comprises a translational motion of the target in a direction of the range measurement or a rotational motion of the target orthogonal to the direction of the range measurement.

6. The system of claim 1, wherein the processor configured to determine, from the range measurement or the Doppler velocity measurement for a point on the target, at least one second aspect of motion of the target comprises the processor configured to determine at least three second aspects of motion of the target.

7. The system of claim 6, wherein the lidar system is configured to generate the range measurement, and wherein the at least three second aspects of motion comprises a translational motion of the target in a direction of the range measurement, a first rotational motion of the target orthogonal to the direction of the range measurement, and a second rotational motion of the target orthogonal to both the direction of the range measurement and the first rotational motion of the target.

8. A method for determining motion of a target, the method comprising:
capturing, via a video imaging system, a plurality of images of a target via a video imaging system;

generating, via a lidar system, a range measurement or a Doppler velocity measurement for a point on the target;

determining, from the plurality of images of the target, at least one first aspect of motion of the target;

determining, from the range measurement or the Doppler velocity measurement, at least one second aspect of motion of the target; and combining the at least one first aspect of motion of the target and the at least one second aspect of motion of the target to determine the motion of the target.

9. The method of claim 8, wherein determining, from the plurality of images of the target, at least one first aspect of motion of the target comprises determining a lateral motion of the target in an image plane of the plurality of images of the target, a vertical motion of the target in the image plane of the plurality of images of the target, or a rotation of the target in the image plane of the plurality of images of the target.

10. The method of claim 8, wherein determining, from the plurality of images of the target, at least one first aspect of motion of the target comprises determining at least three first aspects of motion of the target.

11. The method of claim 10, wherein determining at least three first aspects of motion of the target comprises determining a lateral motion of the target in an image plane of the plurality of images of the target, a vertical motion of the target in the image plane of the plurality of images of the target, and a rotation of the target in the image plane of the plurality of images of the target.

12. The method of claim 8, wherein the lidar system is configured to generate the range measurement, and wherein determining at least one second aspect of motion comprises determining a translational motion of the target in a direction of the range measurement or a rotational motion of the target orthogonal to the direction of the range measurement.

13. The method of claim 8, wherein determining, from the range measurement or the Doppler velocity measurement for the point on the target, at least one second aspect of motion of the target comprises determining at least three second aspects of motion of the target.

14. The method of claim 13, wherein the lidar system is configured to generate the range measurement, and wherein determining at least three second aspects of motion comprises determining a translational motion of the target in a direction of the range measurement, a first rotational motion of the target orthogonal to the direction of the range measurement, and a second rotational motion of the target orthogonal to both the direction of the range measurement and the first rotational motion of the target.

15. A method for determining motion of a target, the method comprising:

capturing, via a video imaging system, a plurality of images of the target via a video imaging system;

generating, via a lidar system, a range measurement or a Doppler velocity measurement for a point on the target; and combining, via a processor, the plurality of images of the target from the video imaging system with the range measurements or the Doppler velocity measurement from the lidar system to determine the motion of the target.

* * * * *